United States Patent [19]

Santangelo et al.

[11] Patent Number: 4,610,242
[45] Date of Patent: Sep. 9, 1986

[54] ENDOSCOPE INSERTION CANNULA ASSEMBLY

[75] Inventors: John A. Santangelo, East Freetown; Michael DiGiantommaso, Brockton, both of Mass.

[73] Assignee: Codman & Shurtleff, Inc., Randolph, Mass.

[21] Appl. No.: 601,456

[22] Filed: Apr. 18, 1984

[51] Int. Cl.$^4$ ............................................. A61B 1/06
[52] U.S. Cl. ..................................................... 128/4
[58] Field of Search ............................... 128/4, 5, 6, 7

[56] References Cited

U.S. PATENT DOCUMENTS

| | | | |
|---|---|---|---|
| 1,397,732 | 11/1921 | Goodloe | 128/7 |
| 1,880,551 | 10/1932 | Wappler | 128/7 |
| 2,584,619 | 2/1952 | Rubens et al. | 128/5 |
| 4,188,942 | 2/1980 | Fehlberg | 128/6 |
| 4,254,762 | 3/1981 | Yoon | 128/4 |
| 4,550,715 | 11/1985 | Santangelo et al. | 128/4 |

Primary Examiner—William H. Grieb
Attorney, Agent, or Firm—Donal B. Tobin

[57] ABSTRACT

An endoscope insertion cannula assembly including an endoscope housing and axially projecting body having an endoscope tip. An adapter is affixed about the endoscope housing, and a guide is affixed about the adapter. A spring and a seal are also affixed about the adapter. The endoscope instrument, together with the associated adapter, spring and guide, are inserted into a cannula housing. A pin on the inside of the cannula housing interacts with an angled slot on the distal surface of the guide to rotate the endoscope instrument into its proper rotational orientation. A hole in a cam surface of the spring then receives the pin on the inside of the cannula housing to control the axial orientation of the tip of the endoscope instrument with respect to the tip of the cannula tube.

5 Claims, 14 Drawing Figures

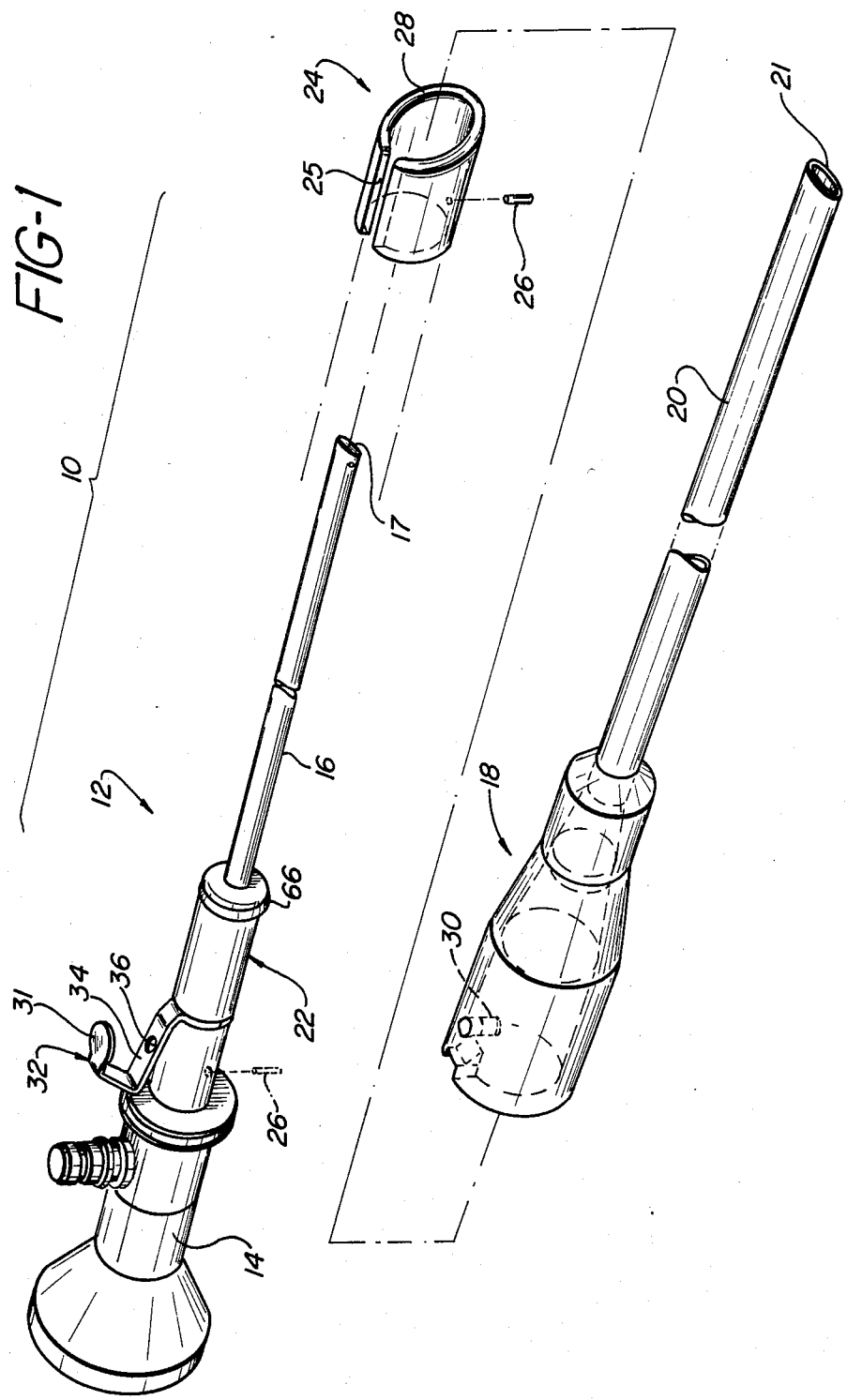

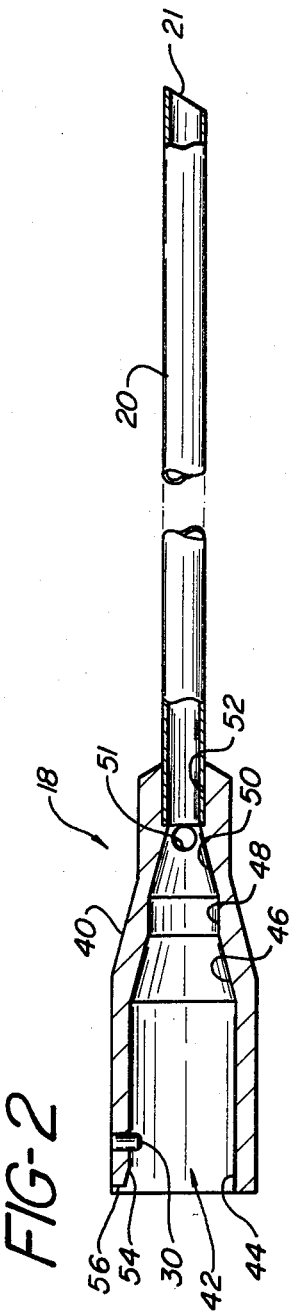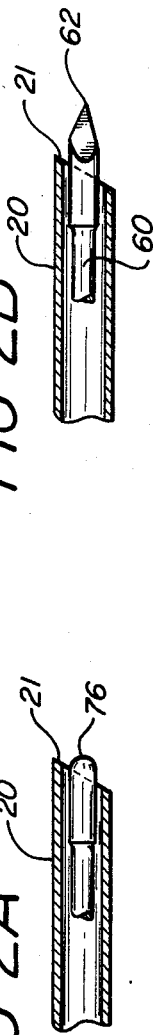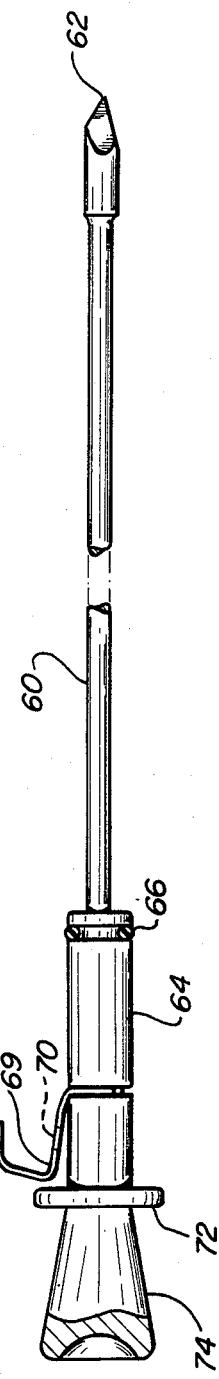

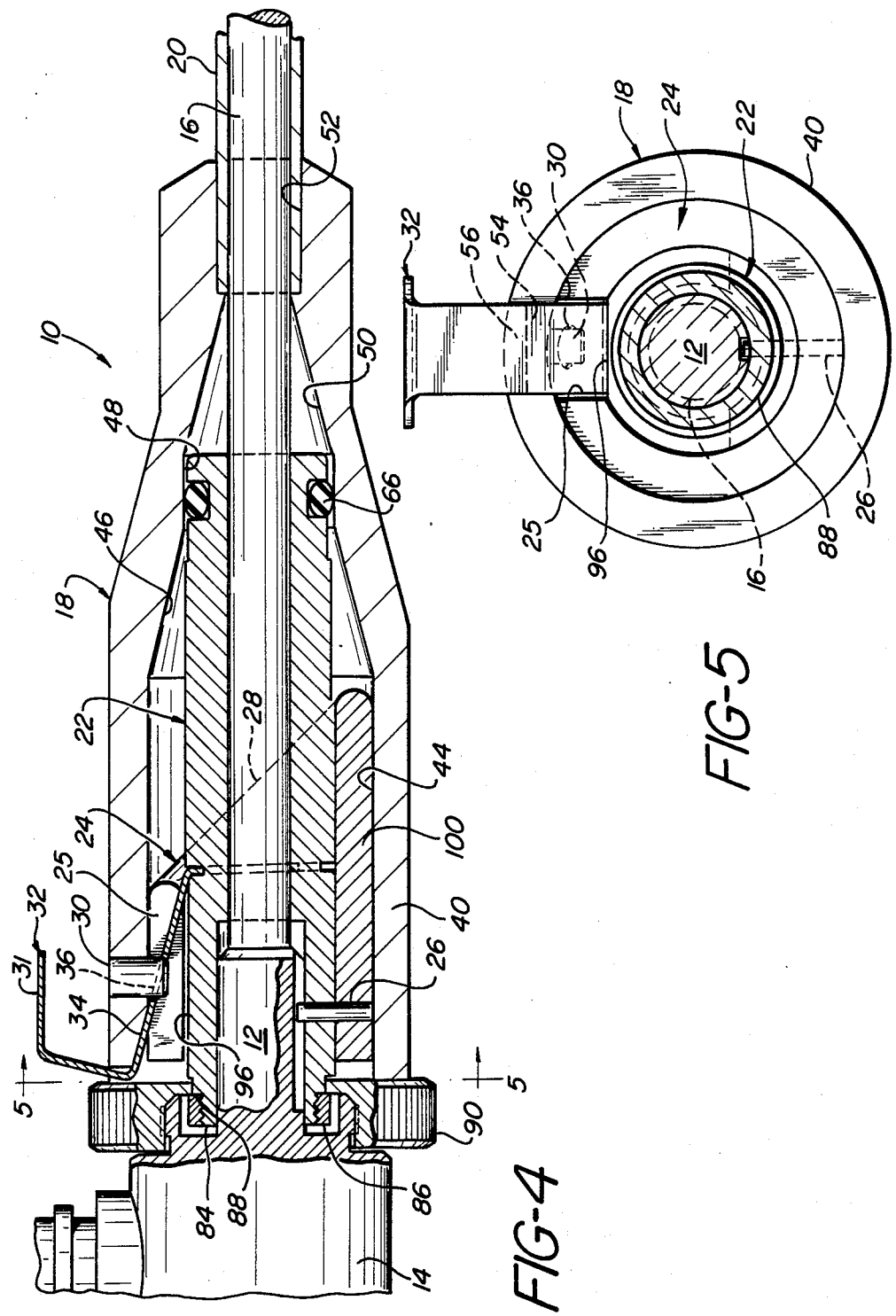

ENDOSCOPE INSERTION CANNULA ASSEMBLY

FIELD OF THE INVENTION

The present invention relates to a cannula assembly for inserting an endoscopy instrument into the body and more particularly to an insertion cannula with a locking mechanism for maintaining the endoscope in a desired rotational and axial position and a sealing mechanism for permitting irrigation or aspiration of the operative site.

BACKGROUND OF THE INVENTION

Endoscopy instruments may be inserted into the body by introducing them into a cannula which has previously been inserted through the skin using a conventional trocar. A cannula is a thin, hollow tube with an open tip on the distal end and a hub of expanded diameter on the proximal end. The hub acts as a guide for directing an instrument or a trocar into the lumen of the tube portion of the cannula. A trocar is an instrument whose sharpened tip projects a short distance beyond the distal end of a surrounding cannula tube. The cannula and the trocar form a small puncture wound in the body as they are inserted through the body tissue. The trocar is then removed leaving the cannula in position with its distal end located in a desired position in the body and with its proximal hub extending outside the body. Thus, the cannula provides an entry site for various endoscopy instruments into the body. A variety of surgical tools and appliances can be inserted through a cannula, for instance a surgical cutting instrument, an aspiration or irrigation tube, or various optical or fiber-optic viewing devices, for example, telescopes which permit the surgeon to inspect the interior of the body.

Particularly with viewing instruments, like telescopes, it is important that the orientation of the optical system inside the body be readily observable from outside the body. Very often the tip of the telescope is designed to look at an angle to its axis rather than straight ahead. The distal end of the telescope is placed at the distal end of the insertion cannula tube so that the telescope will be protected during use by the surrounding tip of the cannula tube, which is usually made of metal or a relatively hard plastic. The distal tip of the cannula tube is also cut at an angle corresponding to the angle of the telescope to permit side viewing. When this side viewing configuration is contemplated, it is important to have the telescope in proper rotational registration with the distal end of the cannula tube. Otherwise, the telescope will focus on the confronting surface of the protective cannula tube rather than at the body structures. It is, thus, important that the precise axial position of the end of the telescope and its rotational orientation be known and controllable.

It is also important to orient the telescope properly with respect to any light source that is inserted into the body so as to reduce glare and shadows.

It is also important in the operating room environment that the telescope or other endoscopy instrument can be easily inserted through the cannula and locked into position so that the surgeon will not have to spend valuable operating time adjusting and aligning the telescope or other instrument.

It is also desirable to have tight sealing engagement between the cannula assembly and the endoscopy instrument to permit irrigation or aspiration of fluid with respect to the operative site. It would be desirable to have an insertion cannula with a locking mechanism which would allow the surgeon to insert a endoscopic instrument, for example a telescope, quickly and easily and be assured that the telescope is in its proper rotational and axial position and that that position could be maintained without constant monitoring and adjusting.

SUMMARY OF THE INVENTION

The present invention provides an insertion cannula assembly with a locking mechanism for holding an endoscopy instrument in a desired orientation with respect to an insertion cannula tube. The locking mechanism orients the endoscopy instrument in a desired rotational orientation regardless of the rotational orientation of the endoscopy instrument before it is inserted into the cannula assembly and locks the instrument into its desired axial and rotational position to maintain that position during use. The locking mechanism also provides a tight fluid seal between the cannula assembly and the endoscope so that fluid may be aspirated from or irrigated into the operative site.

In this patent application the word "proximal" will be used to indicate that portion of a device closest to the end which projects outside the body. The word "distal" will be used to describe that portion of the device closest to the end inside the body.

The endoscope insertion cannula assembly of the present invention includes a cannula housing with a cannula tube extending distally from the housing. The housing is equipped with a port through which irrigation and aspiration fluid can be introduced down the cannula tube. The cannula housing has an expanded internal diameter for accepting an endoscope and its associated adapter, guide and locking mechanism. The adapter is a generally cylindrical device, the exterior dimensions of which are tailored to the interior dimensions of the cannula housing. The interior dimensions of different adapters can be varied to accommodate different endoscopes. The endoscope fits through the center of the adapter and projects into the cannula tube. As mentioned previously, it is important to keep the end of the endoscope instrument, for instance a telescope, in proper rotational and axial register with the end of the cannula tube. A guide is affixed about the exterior of the adapter and includes a distal surface which is disposed at an angle to the center line of the adapter. A pin projects from the inside of the cannula housing. As the endoscope instrument, with its associated adapter and guide, is inserted in the axial direction into the cannula housing and tube, the guide operatively engages the pin. The pin will cause the guide and, therefore, the entire endoscope adapter and endoscope instrument to rotate into a desired rotational orientation and then hold that desired rotational orientation as the instrument is inserted further into the cannula housing to affect locking and sealing.

The distal end of the adapter incorporates an O-ring which mates with a cooperating surface on the interior of the cannula housing to provide a tight seal between the endoscope instrument and the cannula housing. The seal is disposed proximally of the irrigation/aspiration port of the cannula housing.

The locking mechanism includes a spring, which is preferably affixed to the exterior of the adapter, and includes a cam surface which projects from the adapter and extends radially outward as the spring projects in the proximal direction. An appropriate handle is placed on the spring. The cam surface portion of the spring includes a hole through which the pin may project to lock the endoscope instrument in its proper axial orientation.

The guide has an axially extending slot extending from the proximal portion of the angled distal surface of the guide. Thus, as the pin gets to the proper rotational orientation, it enters the slot. The cam surface portion of the spring is then presented to the pin, and the pin slides along the cam surface deflecting the spring until the pin engages the hole. The spring and the pin may be disengaged by depressing the handle portion of the spring.

This apparatus is particularly useful because the endoscope instrument may be inserted into the cannula with one hand and may be easily withdrawn, similarly, with one hand. The user's thumb may be used to depress the handle portion of the spring to disengage the spring from the pin, and then the remainder of the same hand of the user may be used to extract the endoscope instrument from the cannula.

Alternatively, the pin may protrude from the adapter and be positioned in the guide slot. Correspondingly, the spring may be attached to the interior surface of the cannula so that as the endoscopy instrument is inserted into the cannula, the spring and pin will engage in the same fashion as with the alternative embodiment.

These and other features and advantages of the present invention will become apparent from the following detailed description of the preferred embodiment taken in conjunction with the following drawings.

BRIEF DESCRIPTION OF THE DRAWINGS

FIG. 1 shows an exploded perspective view of the endoscope insertion cannula assembly of the present invention;

FIG. 2 shows a cross-sectional view of the cannula assembly and cannula tube;

FIG. 2A shows a sectional view of an obturator extending past the tip of the cannula tube;

FIG. 2B shows the sharpened tip of a trocar extending past the end of the cannula tube;

FIG. 3 shows an elevation of a trocar used with the cannula housing and tube of the present invention;

FIG. 4 shows an assembled, cross-sectional view of the elements of the present invention shown partly in section;

FIG. 5 shows an end view of the apparatus shown in FIG. 4;

DETAILED DESCRIPTION OF THE PREFERRED EMBODIMENT

Figure 6:
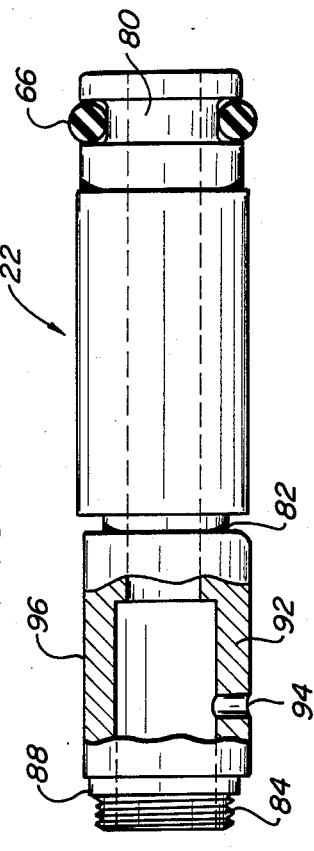
FIG. 6 shows a plan view, partly in section, of part of the present invention.

Referring now to FIG. 1 there is shown an exploded perspective of the cannula assembly of the present invention, generally designated as 10, together with endoscopy instrument 12, preferably a telescope, having a housing 14 and an axially extending body 16 which may be a flexible scope encased in a flexible sheath or a rigid scope encased in a rigid sheath. Cannula housing 18 is adapted to receive an endoscopy instrument 12, and cannula tube 20 projecting from the distal end of cannula housing 18 receives endoscope body 16.

Endoscope 12 is a viewing instrument, and the distal tip 17 of body 16 is cut at a bias to facilitate side viewing. This bias tip can be cut at any convenient angle, but 30°, 45°, or 60° is usually used.

Adapter 22 is a generally cylindrical device which receives the endoscope 12. The internal dimensions of different adapters 22 may be varied to accommodate different endoscopes. The external dimensions of adapters 22 remain the same for different internal dimensions, so that all adapters 22 may be received within the same cannula housing 18. Guide 24 is adapted to fit around the exterior of adapter 22 and is rigidly affixed thereto by, for example, a pin 26. Guide 24 has a generally annular configuration with its distal end surface 28 placed at an angle to the center line of instrument 10 and including an axially extending slot 25 which runs from the proximal portion of distal surface 28 axially along the sidewall of guide 24. Distal surface 28 of guide 24 and a pin 30 projecting from the interior of cannula housing 18 cooperate to control the rotational orientation of guide 24 and, correspondingly, adapter 22 and scope 12 with respect to cannula housing 18.

A spring 32 is fixed to adapter 22 and includes a cam surface 34 having a hole 36 therein. When adapter 22 and guide 24 are assembled, cam surface 34 of spring 32 is disposed in slot 25 on guide 24, so that when endoscope 12, adapter 22 and guide 24 are slid together into cannula housing 18, pin 30 will enter slot 25, interact with cam surface 34 and lodge in hole 36. The dimensions of the cam surface 34, hole 36 and pin 30 and their position on their relative parts are chosen so that the axial position of the tip 17 of endoscope body 16 is properly aligned with the tip 21 of cannula tube 20. The interaction of pin 30 and distal surface 28 of guide 24 provide the proper rotational orientation for the end 17 of endoscope body 16 with respect to the end 21 of cannula tube 20.

The individual parts of instrument 10 will now be discussed in greater detail.

Cannula housing 18 and its associated cannula tube 20 will be discussed in conjunction with FIG. 2. Cannula housing 18 has a surrounding sidewall 40 defining a passage 42 which has several sections. The proximal portion of passage 42 is defined by a generally cylindrical bore 44 which extends into cavity 42 and meets a conic section 46 whose diameter decreases as one moves in the distal direction, which in turn meets a second cylindrical portion 48, which in turn meets a second conical portion 50 of decreasing diameter as one proceeds in the distal direction. A third cylindrical bore 52, having a diameter slightly larger than the smallest diameter of conic portion 50, extends from the distal end of conic portion 50 to the distal end of cannula housing 18. Cylindrical bore 52 receives cannula tube 20. An irrigation port 51 is provided in sidewall 40 in the area of conic portion 50 to provide a means for introducing or aspirating fluid through cannula tube 20.

Pin 30 extends from sidewall 40 in the vicinity of cylindrical bore 44. A small taper 54 is provided on the inside of the proximal end of wall 40 in the vicinity of pin 30 to provide a clearance for spring 32 when pin 30 and spring 32 are engaged. Also, a small cutout 56 is provided in the area of taper 54 for the same reason.

FIG. 3 shows a particular endoscopy instrument that can be used to assist in the insertion of the cannula, called a trocar 60. Trocar 60 has a sharp point 62. When trocar 60 is fully inserted inside cannula housing 18, trocar point 62 projects a short distance beyond the end of cannula tube 20, as shown best in FIG. 2B. The proximal end of trocar 60 has a hub portion 64 much like adapter 22 shown in FIG. 1. Hub portion 64 supports an O-ring 66 and a spring 68 much like the spring 32, as shown on adapter 22 in FIG. 1. Spring 68 has a cam surface 69 and a hole 70 in cam surface 69. Located proximally of spring 68 is a flange 72 and a handle portion 74 for grasping the trocar.

Trocar 60 is inserted into cannula housing 18 until point 62 projects a short distance beyond the tip 21 of cannula tube 20. O-ring 66 will mate with cylindrical portion 48 to provide a tight liquid seal, and hole 70 of cam surface 69 of spring 68 will engage pin 30 to lock trocar 60 and cannula housing 18 together in proper axial orientation. Since it is not important to control the rotational orientation of the trocar tip 62 with respect to cannula tube tip 21, there is no guide like that of guide 24 of FIG. 1 associated with hub 64.

The cannula tube 20 is inserted into the body by using projecting trocar tip 62 to make a small hole in the body, and then inserting cannula tube 20 and trocar 60 together into the desired location within the body, and then removing trocar 60 leaving cannula tube 20 in its desired location within the body. Now that cannula tube 20 is in its proper place inside the body, a variety of endoscopy instruments may be introduced through this cannula tube. As previously discussed when one is using a viewing instrument like a telescope 12, it is important that both the rotational and axial orientation of the end 17 of the telescope body 16 with respect to the end 21 of the cannula tube 20 be in proper registration with one another to facilitate side viewing. If the end 17 of telescope body 16 is not in proper rotational orientation with respect to the end 21 of cannula tube 20, the user could be looking at the inside of cannula tube 20 or could be looking into an illuminating light source.

An obturator may be inserted within cannula tube 20, and its use is shown in FIG. 2A. An obturator is essentially the same as a trocar except it has a blunt end 76.

Figure 7:
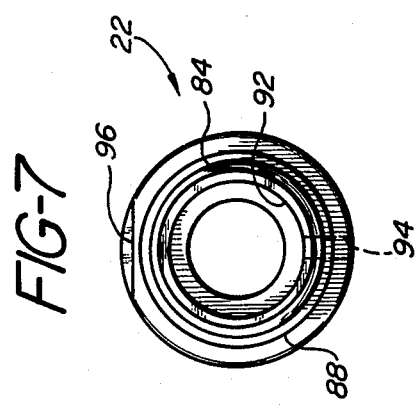
FIG. 7 shows an end view of the apparatus shown in FIG. 6.

Referring now to FIGS. 6 and 7, there is shown the adapter 22. Adapter 22 has a generally cylindrical shape with a first recess 80 near its distal end for receiving an O-ring 66 and a second recess 82 for receiving the mounting prongs of spring 32. The proximal end of adapter 22 includes a threaded flange 84 which is adapted to receive an inner locking ring 86 for holding endoscope housing 14 in place (see particularly FIG. 4). The proximal end of adapter 22 also includes a shoulder 88 for receiving an outer locking ring 90 for holding endoscope housing 14 in place. Adapter 22 has an axially extending cavity running throughout its length defined by the sidewall 92 of adapter 22. A bore 94 in sidewall 92 is adapted to receive pin 26 to hold adapter 22 and guide 24 together (see FIG. 1).

Referring again to FIG. 6, the interior cavity of adapter 22 has a geometry adapted to accept a particular endoscope housing 14 and endoscope body 16. The interior dimensions may vary from one adapter 22 to another, while the exterior dimensions of adapters 22 remain the same so that different endoscope instruments may be used with the same cannula housing 18.

A flat 96 runs along the exterior surface of adapter 22 between shoulder 88 and spring recess 82.

Figure 10:
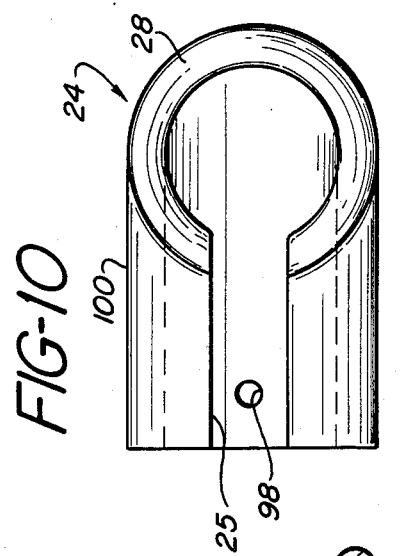
FIG. 10 shows a top view of the apparatus shown in FIG. 8.
Figure 9:
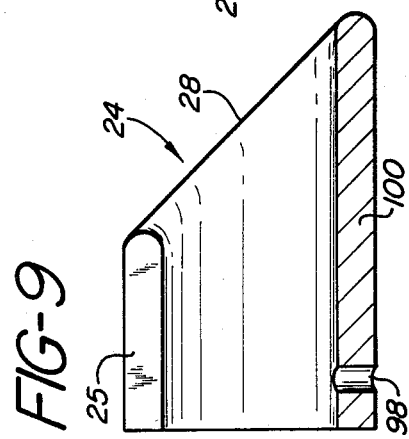
FIG. 9 shows a side view, taken along lines 9—9 in FIG. 8.
Figure 8:
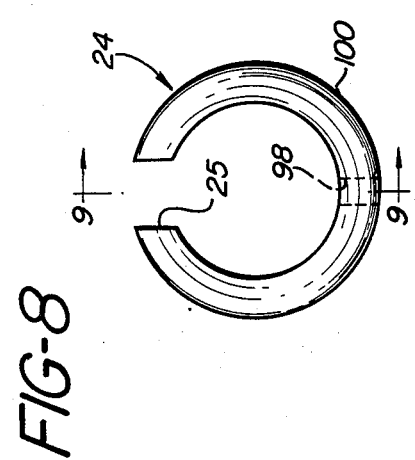
FIG. 8 shows an end view of a part of the present invention.
Figure 11:
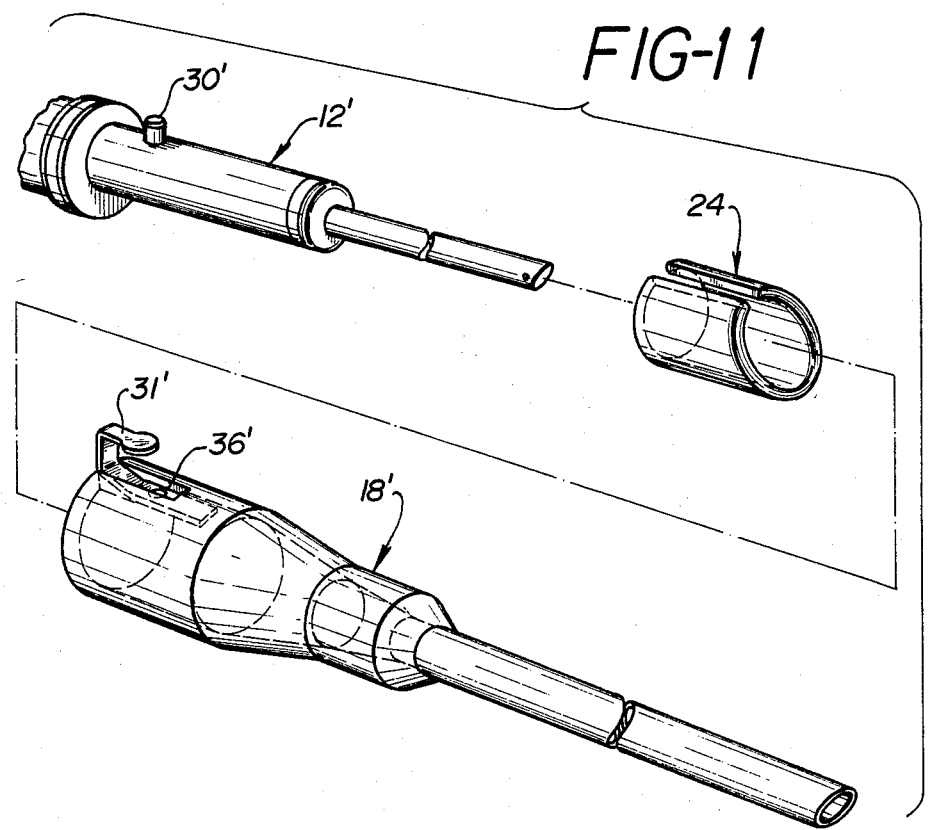
FIGS. 11 and 12 show an alternative embodiment of the invention.
Figure 12:
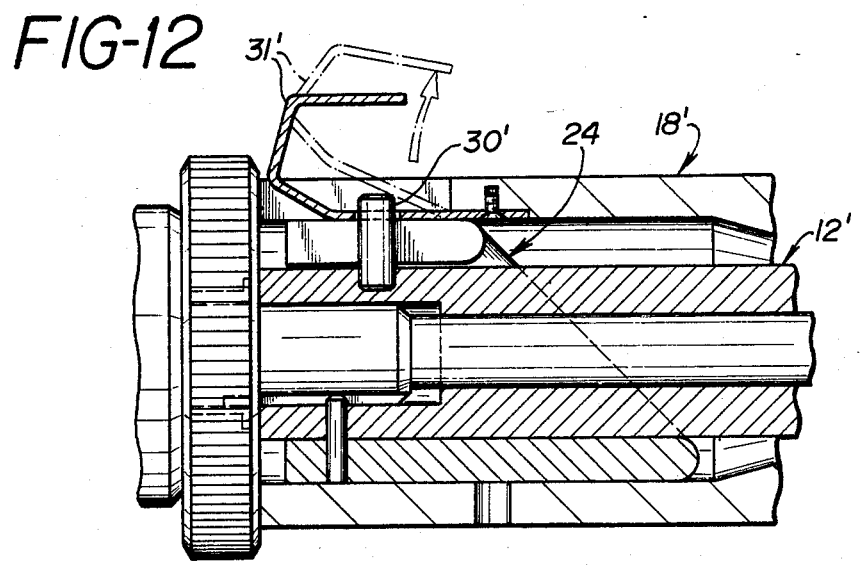

Referring now to FIGS. 8, 9 and 10, there is shown the guide 24 with guide surface 28 and slot 25. Guide surface 28 is preferably cut at an angle of 45° to the axis of instrument 10 and to the axis of guide 24. However, any convenient angle may be used. It is also possible that the guide surface 28 may be concave or convex if desired. A bore 98 in the sidewall 100 of guide 24 is provided to accept pin 26 through which guide 24 is fixed to adapter 22.

Referring now to FIGS. 4 and 5, there is shown an assembled view, partly in section, of the cannula housing 18, guide 24, adapter 22, locking rings 86 and 90, spring 32 and pin 30 together with a part of endoscope housing 14 and endoscope body 16. FIG. 4 shows the relationship between the pin 30 and cam surface 34 of spring 32 with pin 30 in hole 36. It can be seen from FIG. 1 that the end 17 of endoscope body 16 and the end 21 of cannula tube 20 are in correct rotational and axial orientation with respect to one another.

Endoscope 12 can be removed from cannula housing 18 by the user, using only one hand. The user grasps endoscope housing 14 in his palm, placing his thumb on the handle portion 31 of spring 32, and depresses handle 31 so as to disengage hole 36 from pin 30. The user then merely extracts endoscope housing 14 and its associated endoscope body 16 from cannula housing 18.

The operation of endoscopy instrument cannula assembly 10 will now be described principally in connection with FIGS. 1 and 4. It can be seen that as endoscopy instrument 12, with its associated adapter 22 and guide 24 attached to it, is inserted into cannula housing 18, angle-cut proximal end surface 28 of guide 24 will engage pin 30 and interact therewith to rotate instrument 12 until pin 30 is aligned with guide slot 25. End surface 28 acts as an orienting mechanism for making sure that pin 30 and, hence, instrument 12 are aligned in the proper rotational orientation with guide slot 25 regardless of the orientation of instrument 12 when it is first inserted into cannula 18. Referring now particularly to FIG. 4, it can be seen that as pin 30 enters guide slot 25, it will begin to interact with cam surface 34 of spring 32 and depress cam surface 34 until pin 30 enters hole 36. The interaction of pin 30 and hole 36 controls the axial orientation of endoscope 12 with respect to cannula housing 18.

In an alternative embodiment, it is possible that pin 30 could be disposed on endoscope housing 14 and guide surface 28, and slot 25 could be disposed on the interior of cannula housing 18. Spring 32, or an alternative embodiment thereof, could also be disposed on the interior of cannula housing 18 to provide a locking mechanism for controlling the axial orientation of the endoscope instrument with respect to cannula housing 18.

It will be appreciated that the present invention provides a convenient and effective method for quickly introducing an endoscopy instrument into a cannula assembly and automatically providing correct and locked rotational and axial alignment for the instrument with respect to the tip of the cannula. The present invention has been described in conjunction with certain preferred embodiments. Those skilled in the art will appreciate that many modifications and changes may be made to the preferred embodiment without departing from the scope of the present invention. It is, therefore, not intended to limit the present invention except as set forth in the appended claims.

I claim:

1. An assembly for permitting an endoscope instrument element to be inserted through a cannula element into the body in known orientation and for locking said cannula element and said endoscope element in that known orientation during use comprising:

means cooperatively associated with said endoscope instrument element and with said cannula element for directing the rotational orientation and controlling the axial position of one element with respect to the other, said cooperative means including:

a protrusion from one of said cooperating elements:

a guide surface on said other element for operatively engaging said protrusion to direct the rotational orientation of said protrusion as said endoscope instrument element is inserted into said cannula element regardless of the initial relative rotational orientation therebetween;

said guide surface disposed at an angle to the axis of said other element and including a slot for receiving said protrusion;

spring biased locking means for restraining the protrusion in a desired axial position, said locking means including a cam surface which moves against said protrusion as said endoscope element is inserted into said cannula element, said cam surface adapted to move out of the way as said endoscope element moves into said cannula element and then to return toward its original position as said protrusion reaches its desired axial position; and wherein said endoscope element includes an adapter having exterior dimensions fitting said cannula element and capable of having different interior dimensions for adapting different endoscope instruments for use in the same cannula element;

whereby said instrument element is positioned in its desired rotational orientation and axial position during use.

2. The apparatus of claim 1 wherein said protrusion includes a pin projecting from the inside of said cannula element and said endoscope instrument element includes a generally cylindrical adapter having a distal end projecting into said cannula and a proximal end extending outside of said cannula, the proximal end of said adapter adapted to receive an endoscope telescope, said adapter having an axial opening extending entirely therethrough for receiving an endoscope telescope, said adapter including sealing means cooperating with the interior walls of said cannula element for providing a tight liquid seal between the interior of said cannula and the exterior of said adapter;

said endoscope instrument element further including a guide means disposed about the periphery of said adapter and affixed thereto and having a distal end disposed at an angle to the axis of said adapter and defining a surface for engaging said protrusion, said guide means further including an axially extending slot extending from the proximal portion of said angled distal surface.

3. The apparatus of claim 2 wherein said angled cut distal end of said guide means includes a straight bias cut.

4. The apparatus of claim 1 wherein:

said spring biased locking means includes a strip of spring material affixed to said endoscope instrument element and extending axially therealong and aligned in the slot of said guide means;

said spring strip extending radially outwardly from the axis of said endoscope instrument element as one moves proximally along said endoscope instrument element, said spring strip presenting a cam surface to said protrusion;

said spring strip having a hole therethrough for receiving said protrusion, the interaction of said protrusion and said hole defining the axial position of said endoscope instrument element with respect to said cannula element.

5. The apparatus of claim 1 wherein said protrusion extends from said endoscope instrument element and wherein said locking means includes a strip of metal affixed to the interior surface of said cannula element.

* * * * *